(12) United States Patent
Ullah et al.

(10) Patent No.: US 7,175,856 B2
(45) Date of Patent: Feb. 13, 2007

(54) PALATABLE ORAL SUSPENSION AND METHOD

(75) Inventors: Ismat Ullah, Cranbury, NJ (US); Gary J. Wiley, Jackson, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 380 days.

(21) Appl. No.: 10/386,199

(22) Filed: Mar. 11, 2003

(65) Prior Publication Data

US 2003/0187019 A1 Oct. 2, 2003

Related U.S. Application Data

(60) Provisional application No. 60/363,704, filed on Mar. 12, 2002.

(51) Int. Cl.
*A61K 9/14* (2006.01)
*A01N 43/42* (2006.01)

(52) U.S. Cl. ............................ 424/489; 514/312
(58) Field of Classification Search ............... 424/489
See application file for complete search history.

(56) References Cited

U.S. PATENT DOCUMENTS

| | | | |
|---|---|---|---|
| 4,656,027 A | | 4/1987 | Sjöovist |
| 4,831,058 A | * | 5/1989 | Pankhania et al. .......... 514/570 |
| 4,865,851 A | | 9/1989 | James et al. |
| 5,023,257 A | * | 6/1991 | Pollinger et al. ...... 514/253.03 |
| 5,152,986 A | * | 10/1992 | Lange et al. ............. 424/78.14 |
| 5,262,179 A | * | 11/1993 | Gregory et al. ............. 424/489 |
| 5,409,711 A | | 4/1995 | Mapelli et al. |
| 5,409,907 A | * | 4/1995 | Blase et al. .................... 514/54 |
| 5,498,447 A | | 3/1996 | Nishii et al. |
| 5,653,993 A | | 8/1997 | Ghanta et al. |
| 5,695,784 A | * | 12/1997 | Pollinger et al. ........... 424/495 |
| 5,948,422 A | | 9/1999 | van Kourtrik et al. |
| 5,972,379 A | | 10/1999 | Guo et al. |
| 6,025,370 A | | 2/2000 | Todo et al. |

FOREIGN PATENT DOCUMENTS

| | | |
|---|---|---|
| EP | 0 069 097 A2 | 10/1982 |
| EP | 0 069 097 B1 | 10/1982 |

OTHER PUBLICATIONS

Remington's Pharmaceutical Sciences, 18th ed., 1990, pp. 1290-1292.

* cited by examiner

*Primary Examiner*—S. Tran
(74) *Attorney, Agent, or Firm*—Burton Rodney

(57) ABSTRACT

A drug formulation in the form of a dry powder is provided which when mixed with water forms a palatable oral suspension substantially free of bitter taste, the dry powder being formed of a drug, preferably des-quinolone, which in solution has a bitter taste, and a pH modifying agent which is preferably an alkaline material such as L-arginine, where upon mixing the dry-powder in water causes the drug to have reduced solubility or precipitate in-situ to form a palatable oral suspension essentially free of bitter taste.

An oral suspension, methods for making same and a method for masking the bitter taste of drugs employing one or more pH modifying agents are also provided.

13 Claims, No Drawings

PALATABLE ORAL SUSPENSION AND METHOD

This application claims priority from U.S. Provisional Application No. 60/363,704 filed Mar. 12, 2002 which is incorporated herein by reference.

The present invention relates to a pharmaceutical formulation in the form of a palatable oral suspension which includes suspended particles of a readily water soluble drug such as des-quinolone antibacterial agent, whose normally bitter taste is masked, to a dry powder formed of the above drug and a pH modifying agent which when mixed with water undergoes in-situ reduction in solubility or precipitation to form a suspension of such powder which is substantially free of bitter taste, to a method for preparing such oral suspensions, and to a method for masking the taste of orally administered readily soluble bitter tasting drugs without the need for insoluble polymer or wax coatings or microencapsulation techniques.

BACKGROUND OF THE INVENTION

Patient compliance is a major consideration when pharmaceutical formulations in the form of oral solutions are to be employed. Generally, oral solutions of drugs will have a bitter or otherwise unpalatable taste. In order to make oral liquid formulations more palatable, it has been suggested to mix drug in powder form with various polymeric or wax coating agents or to microencapsulate the particles of the drug so that they may be suspended in and prevented from solubilizing in liquid for oral administration. As will be seen hereinafter, these techniques are complex, expensive and fraught with various processing and drug delivery problems.

U.S. Pat. No. 4,656,027 to Sjoovist et al. (Astra Lakemedel) discloses an oral pharmaceutical preparation which is formed by encapsulating a mixture of drug (which is normally unpalatable) and a basic substance, in a water-insoluble polymer the resulting microcapsules of which are insoluble at high pH, and adding water hereto to form the oral preparation. In an alternative embodiment, the basic substance is mixed with already encapsulated drug. Sjoovist et al indicates that the combination of the use of encapsulated drug and basic substance effectively masks the taste of the drug. Examples of basic substances employed include various hydrogen phosphates, trisodium citrate, magnesium hydroxide.

European Patent Application 0069097 (Astra Lakemedel) discloses an oral suspension formed of microencapsulated bacampicillin HCl and a basic substance such as a carbonate, for example, sodium bicarbonate, a phosphate or a citrate, whereby the otherwise bitter taste of the bacampicillin HCl is masked by encapsulating polymer and basic substance.

U.S. Pat. No. 4,865,851 to James et al discloses coating of particles of cefuroxime axetil coated with a lipid to mask bitter taste, which particles may be mixed with water to form an aqueous suspension.

U.S. Pat. No. 5,498,447 to Nishii et al discloses the coating of a wax on particles of medicament to mask unpleasant and bitter tastes.

U.S. Pat. No. 5,409,711 to Mapelli et al. (Eurand International) discloses to a pharmaceutical formulation for oral administration which includes a core containing a drug that is coated with a polymeric membrane which is soluble only at a pH of 5 or greater. An acidic compound is mixed with the coated core for reducing dissolution of the membrane in the oral cavity. The drug will be released only when the coated cores have passed through the stomach and reached the intestine where there is a pH equal to or greater than 5. The addition of the acidic compound agent is used to reduce the solubility of the polymeric membrane. The polymer membrane, in turn, provides taste masking qualities.

U.S. Pat. No. 5,653,993, to Ghanta et al. (Eurand America) teaches a procedure for microencapsulation of an NSAID drug with cellulose acetate phthalate and gelatin to mask the taste of the drug.

In each of the above patents and applications, the formulations prepared require extra processing and a polymeric physical membrane or barrier in the form of a film or encapsulation which provides the insolubility and taste masking components. The major drawback to use of a polymeric membrane is that the process involved is complicated and expensive and the dissolution of the drug may be incomplete so that release of the drug active may be inhibited resulting in lower bioavailability.

Conventional taste masking techniques such as sweeteners and flavoring agents are often used in addition to encapsulation. However, many traditional sweeteners are not effective in masking particularly unpleasant tasting drugs without the addition of another taste masking mechanism. A less complex approach for taste masking readily soluble actives would thus be a useful addition to the art.

U.S. Pat. No. 6,025,370 to Todo et al. (Toyama Chemical Co.) discloses various quinolonecarboxylic acid derivatives which covers des-quinolone (1-cycloproply-8 -(difluoromethoxy)-7-[(1R)-1-methyl-2,3-dihydro-1H-5-isoindolyl]-4-oxo-1,4-dihydro-3-quinolonecarboxylic acid methanesulfonate monohydrate). This is a readily water soluble compound with bitter taste.

SUMMARY OF THE INVENTION

In accordance with the present invention, a novel oral suspension of a normally unpalatable drug is provided which suspension is substantially devoid of bitter taste, and is formed of particles of a readily soluble drug which normally is associated with a bitter taste when in solution, and water to form an oral suspension, which particles of drug are rendered and maintained substantially insoluble in the oral suspension so that the bitter taste of the drug is masked without use or need for polymer or wax coating or microencapsulation. The particles of drug are rendered and maintained in substantially insoluble form preferably through use of one or more pH modifying agents which are mixed with particles of the drug. Thus, when the drug and pH modifying agent are mixed with water for constitution and suspension, the pH modifying agent adjusts suspension pH to reduce or minimize solubility of the drug and thus reduces or masks the bitter taste normally associated therewith.

In effect, when drug and pH modifier are mixed with water to form an oral suspension, the drug precipitates in-situ and remains substantially insoluble and thus is substantially free of bitter taste until after the oral suspension is ingested.

The oral suspension of the invention will contain one or more pH modifying agents in an amount to render and maintain the drug substantially insoluble in water.

In addition, in accordance with the present invention, a method is provided for preparing an oral suspension of a drug which normally in solution is associated with a bitter taste, which includes the steps of providing a drug which in solution is associated with a bitter taste, admixing the drug with one or more pH modifying agents capable of generating a pH environment in water to effect reduction in solubility or precipitation of drug and maintaining drug in substantially insoluble or less soluble form, and admixing the drug and pH modifier with water to form an oral suspension of the drug which when ingested will be free or essentially free of bitter taste.

Still further in accordance with the present invention a dry drug powder formulation is provided which when admixed with water will form an oral suspension substantially free of bitter taste, which dry drug powder formulation is formed of a drug which in solution form is associated with a bitter taste, and one or more pH modifying agents therefor which renders and maintains the drug insoluble or essentially insoluble in water to thereby effectively masking the bitter taste of the drug.

The dry drug powder formulation of the invention will contain one or more pH modifying agents in an amount to render and maintain the drug substantially insoluble in water.

Further in accordance with the present invention, a method is provided for masking the bitter taste of a drug which in soluble form is associated with a bitter taste, which method includes the step of employing the drug in particulate form together with one or more pH modifying agents so that when the drug and pH modifier are admixed with water, the pH modifier will provide a pH environment which renders and maintains the drug substantially insoluble, in suspension, whereby the bitter taste of the drug is masked and/or substantially reduced.

In a preferred embodiment of the invention, the drug employed in the oral suspension of the invention in conjunction with the pH modifying agent is des-quinolone antibacterial agent.

DETAILED DESCRIPTION

As described above, the present invention involves masking the bitter taste of a readily water-soluble drug through the use of one or more pH modifying agents, where upon constitution of the drug with water, the pH modifying agent generates a pH environment to form an aqueous suspension of in-situ precipitated drug or reduced solubility of drug which results in substantial taste-masking of the drug. The drug remains substantially insoluble upon ingestion until it reaches the pH at which it is soluble, such as acidic pH in the stomach or alkaline pH in the small intestine, as the case may be. Preferably, the pH modifying agent is an alkaline material which raises the pH of the suspension for a drug normally soluble in a neutral or acidic environment. Once the drug is ingested the lower pH of the stomach provides the necessary conditions for the drug to re-dissolve into solution and be absorbed by the body.

This taste masking technique is an especially useful advancement in the art for drugs which are readily soluble in water and are bitter tasting. As can be appreciated by those skilled in the art, a readily soluble bitter tasting drug presents a substantial challenge when attempting to develop palatable, orally administered liquid formulations. It should be further appreciated that the powder formulation of the present invention comprises a mixture of the readily soluble drug in particulate form and one or more pH-modifying agents. There is no need for microencapsulation or coating of the bitter drug active with various polymers or waxy materials or utilization of an insoluble form of the drug inasmuch as the drug interacts with the pH modifying material to create an essentially insoluble tasteless moiety.

During the manufacture of the oral suspension of the invention, costly and complex coating or microencapsulation steps are not utilized or required. Instead, the pH-modifying agent is pre-selected so as to provide a pH at which the drug is minimally or near minimally soluble when the powder formulation is constituted with water. Thus, upon ingestion of the suspension, the pH environment to which the drug is subjected when it is swallowed renders the drug insoluble, masking most or all of the bitter taste. When the suspension reaches the low pH of the stomach, or the pH of the intestines, as the case may be, the drug, now soluble at the new pH, goes into solution and is thereafter systemically utilized.

It should be appreciated that bitter tasting drugs which are even slightly soluble in water will exhibit bitterness.

Drugs suitable for use with the present invention include any drugs which are soluble in water, but which are substantially insoluble at a higher or lower pH and whose solubility can be decreased by addition of a pH modifying agent which causes reduced solubility or in-situ precipitation of drug upon constitution with water. In this way, the addition of a pH modifying agent renders the drug substantially insoluble and, therefore substantially tasteless, in mouth and throat areas, but soluble and available to the system of the patient when the pH of the stomach or the intestines alters the pH environment realized by the drug.

While the present invention provides the greatest improvement for readily water soluble drugs, any drug where decreasing solubility in water will enhance taste masking, will benefit from utilizing the concepts disclosed herein and are considered as part of the invention.

Agents for modifying pH can be any convenient pH modifying agent capable of providing reduced solubility and/or an in-situ precipitate of the desired drug when constituted with water. Depending upon the nature of the drug employed the pH modifying agent may be an acidic agent which provides a pH of the suspension lower than the drug pH in water, or an alkaline agent which provides a pH of the suspension greater than the drug pH in water.

More than one pH modifying agent can also be used in combination.

Classes of drugs for which the present invention is useful which form a precipitate with an alkaline pH modifying agent include, but are not limited to, quinolone- or naphthyridone-carboxylic acid derivatives, and other antibacterial agents such as norfloxacin, ciprofloxacin, or ofloxacin. Preferred are quinolone- or naphthylidone-carboxylic acid derivatives disclosed in U.S. Pat. No. 5,935,952 and U.S. Pat. No. 6,025,370 each to Todo et al, each of which is incorporated herein by reference.

A preferred drug is a quinolone-carboxylic acid of the formula:

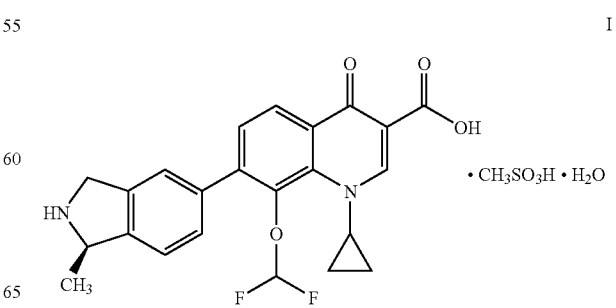

1-Cyclopropyl-8-(difluoromethoxy)-7-[(1R)-1-methyl-2,3-dihydro-1H-5-isoindolyl]-4-oxo-1,4-dihydro-3-quinolinecarboxylic acid methanesulfonate monohydrate (also referred to herein as des-quinolone).

The des-quinolone is a mesylate salt with water solubility of about 17.4 mg/ml at ambient room temperature. A solution of the des-quinolone is bitter with a lingering bitter after taste. It has been found that the solubility of the des-quinolone decreases significantly upon neutralization to form a zwitterion, with minimum solubility of about 0.07 mg/mL at pH range from about 5.5 to 8. In accordance with the invention, where the preferred des-quinolone is mixed with an alkaline agent, preferably L-arginine, upon constitution with water, L-arginine causes in-situ formation of an insoluble zwitterion, which is relatively tasteless and hence easier to mask taste.

Examples of readily soluble drugs which form a precipitate with an acid pH modify agent, include but are not limited to, sodium cloxacillin monohydrate, sodium dicloxacillin monohydrate or sodium ifetroban.

Preferred alkaline pH modifying agents for use with the quinolone- and naphthylidone-carboxylic acid derivatives above, including the preferred des-quinolone or other acidic drugs, as mentioned above, include, but are not limited to, L-lysine, L-arginine, sodium citrate and magnesium hydroxide. The more preferred alkaline pH modifying agents for these preferred acidic drugs are sodium citrate and L-arginine. L-arginine is the most preferred.

Examples of acidic pH modifying agents suitable for use herein include, but are not limited to, fumaric acid, citric acid, tartaric acid, malic acid, maleic acid or succinic acid.

By the term "readily soluble" or "readily water soluble" is meant that the drug will be substantially, or at least partially, soluble in water such that any bitter taste inherent in the drug will be apparent upon oral administration. It is believed that the greater the solubility in water, the more beneficial will be the taste masking effects of the present invention. The solubility of the drug is also dependent on the availability of the counter-ions in solution which is important when selecting pH modifying agents that may have counter-ions which can offset the intended affects of decreasing solubility.

The term "substantially insoluble" when used to describe the effect of the pH modifying agent on the drug refers to the rendering of the drug, upon addition of water, in an at least partially insoluble state where at least some of the drug is precipitated. It is preferred that upon addition of water a maximum amount of drug be precipitated with a minimum amount of drug remaining in solution thereby resulting in a maximum reduction in bitter taste of the drug. As long as some of the drug is precipitated, the bitter taste of the drug will be reduced.

The term "in-situ precipitate" when used to describe the state of the drug in suspension refers to the rendering of some or substantially all of the drug in precipitated form upon addition of water.

The term "substantially free of bitter taste" or "essentially free of bitter taste" or similar terms when used in conjunction with the drug treated with pH modifying agent, refers to drug whose taste is modified to reduce or substantially eliminate bitter or other unpleasant taste. Thus, the taste of a suspension of such drug will be tolerated or found to have acceptable palatability by the patient.

The pharmaceutical powder formulation of the present invention may optionally include excipients and other ingredients such as one or more sweeteners, flavors, additional taste modifiers, suspending agents, glidants, antioxidants, preservatives and other conventional excipients as needed.

The oral suspension of the invention may optionally include one or more antioxidants, if necessary, taste modifiers, sweeteners, glidants, suspending agents, and preservatives.

As will be appreciated, the above optional ingredients may be added to the powder formulation of the invention, and/or to the oral suspension of the invention.

Antioxidants suitable for use herein include any convenient agents known in the art for this purpose such as sodium metabisulfite, sodium bisulfite, cysteine hydrochloride, citric acid, succinic acid, ascorbic acid, sodium ascorbate, fumaric acid, tartaric acid, maleic acid, malic acid, EDTA with sodium metabisulfite or sodium bisulfite being preferred.

Antioxidants may be employed in an amount which will protect the drug of choice from oxidation as will be apparent to one skilled in the art.

Sweeteners for use in the formulations of the invention may be any convenient agents known in the art for this purpose and may be selected from any compatible sweetener groups such as natural sweeteners like sucrose, fructose, dextrose, xylitol, sorbitol, or manitol, as well as artificial sweeteners such as aspartame, acesulfame K and sucrolose. Xylitol and aspartame are preferred sweeteners.

Flavors and flavor modifiers or taste modifiers can also be used to further improve the taste and can be any convenient agents known in the art for this purpose and include, but are not limited to, orange flavor, vanilla flavor, licorice flavor, orange vanilla flavor, creme de mint, cherry flavor, cherry vanilla flavor, berry mix flavor, passion fruit flavor, mandarin orange flavor, bubble gum flavor, tropical punch flavor, juicy compound for grape, grape flavor, artificial grape flavor, grape bubble gum flavor, and tutti-frutti-flavor, and combinations thereof, with artificial grape flavor being preferred.

Glidants can also optionally be used. The preferred glidant employed for this formulation is silicon dioxide although other suitable glidants include talc and titanium dioxide.

Suspending agents can be any convenient agents known in the art for this purpose and can be selected from xanthan gum, guar gum, hydroxypropylmethyl cellulose, hydroxypropyl cellulose, polyvinyl pyrrolidone, alginates, and sodium carboxylmethylcellulose with sodium carboxylmethylcellulose (Na CMC) being preferred. Suspending agents may be employed in an amount within the range from about 0 to about 20% by weight of the powder formulation, and from about 0 to about 10% by weight of the oral suspension.

Preservatives can be any convenient agents known in the art for this purpose and can be selected from the group consisting of any compound compatible with drug actives such as methylparaben and propylparaben, benzoic acid, sodium benzoate, potassium sorbate, with methylparaben being preferred.

Where the drug employed is des-quinolone, it is preferred that the pH modifier employed be L-arginine. To inhibit possible oxidation of the preferred des-quinolone, the formulation may include an antioxidant in the formulation, preferably sodium bisulfite. In addition, the formulation may include sweeteners such as xylitol and aspartame, and taste modifiers, and various flavoring agents. The formulation will also preferably contain one or more powder glidants such as silicon dioxide, one or more suspending agents such as carboxymethyl cellulose, and one or more preservative such as methyl paraben.

The drug can be included in any convenient and suitable dosage strength or concentration. For example, the des-quinolone can be administered to an adult in a dose of from 50 to 1000 mg per day in one or more single or divided doses. The oral suspension may contain the preferred des-quinolone in a concentration from 10 mg to 400 mg/5 ml, more preferably, 100 to 200 mg per 5 ml (~40 mg/mL).

Other quinolone antibacterial agents such as norfloxacin, ciprofloxacin or ofloxacin may be employed in amounts as set out in the Physician's Desk Reference.

The powders of this formulation can be prepared by any mixing and/or blending techniques known in the art. As can be appreciated by those skilled in the pharmaceutical art, it is essential to obtain a high degree of uniformity in any such mixing or blending so that the pH modifying agent and other agents, such as preservatives and antioxidants are uniformly dispersed throughout the powder.

The following table sets out preferred embodiments of the invention. The ranges set out may be for the broad class of each ingredient set out or the preferred ingredient set out:

| PREFERRED CONSTITUTED FORMULATION (mg/5 ml) | | |
|---|---|---|
| Ingredient (preferred) | Range mg of Ingredient | Preferred Range mg of Ingredient |
| Drug (Des-quinolone) | 10 to 600 | 12.7 to 508 |
| pH modifier (L-Arginine) | 3 to 200 | 4.2 to 170 |
| Antioxidants (Sodium bisulfite) | 0 to 20 | 0.4 to 14 |
| Suspending Agents (carboxymethyl cellulose) | 0 to 24 | 6 to 10 |
| Powder Glidants (Silicon dioxide) | 0 to 100 | 20 to 60 |
| Preservatives (Methylparaben) | 0 to 16 | 6 to 10 |
| Sweeteners (Xylitol) (Aspartame) | 0 to 3000 / 0 to 400 | 2500 to 2800 / 50 to 300 |
| Flavors and Taste Modifiers | 0 to 200 | 10 to 100 |

The following Examples represent preferred embodiments of the present invention.

EXAMPLE 1

Dry Powder and Suspension Formulation Containing Des-Quinolone (3.301 Kg blend for 100 mg/5 ml strength)

A dry powder containing des-quinolone was prepared by a blend-mill-blend process. The following ingredients were blended in a tumbling type blender for 15 minutes: Des-quinolone (126.9 g), sodium bisulfite (3.5 g, 200 mesh or equivalent screened), silicon dioxide (20 g), aspartame (200 g), L-arginine (42 g), sodium CMC (8.0 g), methylparaben (8.0 g), Magnasweet 100 (18.0 g), Natural Special Compound (30.0 g), grape flavor (45.0 g) and xylitol (2800.0 g). The powder was discharged from the blender and was Fitz milled through a #00 plate, hammers forward, high speed and medium feed rate. The milled powder was then reblended in a tumbling type blender for 20 minutes. The powder was discharged from the blender and filled into HDPE 60 cc bottles for desired fill weight. Each bottle when constituted with appropriate amount of water produced a palatable suspension with drug concentration of 100 mg/5 ml.

EXAMPLES 2 TO 5

Formulations of a Pediatric Powder for Oral Suspension (POS) Containing Des-Quinolone and L-Arginine.

EXAMPLE 2

(3.317 kg blend for 200 mg/5 ml strengths)

Preparation of Dry Powder
A dry powder containing des-quinolone was prepared by blend-mill-blend process as described in Example 1.

| COMPOSITIONS OF 10, 100, 200 AND 400 MG/5 ML PRODUCTS, as Free Base. (amounts in g/5 ml) | | | | |
|---|---|---|---|---|
| | Example No. | | | |
| Ingredients | 2<br>10 mg/5 ml | 3<br>100 mg/5 ml | 4<br>200 mg/5 ml | 5<br>400 mg/5 ml |
| Des-quinolone (preferred) | 0.0127<br>(10 mg activity) | 0.1265<br>(100 mg activity) | 0.2540<br>(200 mg activity) | 0.5080<br>(400 mg activity) |
| Sodium Bisulfite | 0.0004 | 0.0035 | 0.0070 | 0.0140 |
| Silicon Dioxide | 0.0200 | 0.0200 | 0.0600 | 0.0600 |
| Aspartame | 0.0500 | 0.2000 | 0.3000 | 0.3000 |
| L-Arginine | 0.0042 | 0.0420 | 0.0850 | 0.1700 |
| Sodium CMC | 0.0080 | 0.0080 | 0.0080 | 0.0080 |
| Methylparaben | 0.0080 | 0.0080 | 0.0080 | 0.0080 |
| Magnasweet 100 | 0.0100 | 0.0180 | 0.0200 | 0.0220 |
| Nat. Special Compound | 0.0300 | 0.0300 | 0.0300 | 0.0300 |
| Artificial Grape Flavor | 0.0450 | 0.0450 | 0.0450 | 0.0450 |
| Xylitol | 2.8000 | 2.8000 | 2.5000 | 2.5000 |
| Net Weight | 2.9883 | 3.301 | 3.317 | 3.665 |

Each formulation when constituted with appropriate amount of water produced a palatable suspension with drug concentration as indicated.

EXAMPLE 6

(200 mg/5 mL as Free Base upon Appropriate Constitution)

A 215 kg powder blend of a des-quinolone dry powder formulation of the invention was prepared as follows.

The materials listed below were passed through a Fitz mill equipped with a 2B plate (hole size 2.74 mm), medium speed, and impacts forward. Milling was started with a portion of xylitol, followed with milling of the rest of the ingredients, which were combined with xylitol in the hopper while being milled. The milled material was collected in polyethylene lined fiber drums. The materials milled were:

| | |
|---|---|
| Xylitol (Xylisorb 300) | 162.0664 Kg |
| Des-quinolone | 16.4337 Kg |
| Sodium Bisulfite (200 mesh equivalent milled) | 0.4539 Kg |
| Silicon Dioxide | 3.8898 Kg |
| Aspartame Powder | 19.4493 Kg |

-continued

| | |
|---|---|
| L-Arginine | 5.5107 Kg |
| Sodium Carboxymethyl Cellulose | 0.5186 Kg |
| Methylparaben | 0.5186 Kg |
| Magnasweet 100 | 1.2967 Kg |
| Natural Special Compound | 1.9449 Kg |
| Artificial Grape Flavor | 2.9173 Kg |

The above milled materials were transferred to a 20 cu. ft. V-Blender and blended for 15±2 minutes at 10 RPM. This blended material was then milled through a Fitz mill equipped with a #00 plate (hole size 0.61 mm), impact forward, at high speed. This milled material was then transferred to a 20 cu. ft. V-Blender and blended for 20±3 minutes at 10 RPM. The blend was collected in polyethylene lined fiber drums, and was subsequently filled into appropriate size bottles.

Upon constitution with water, a suspension of des-quinolone was formed which was substantially free of bitter taste.

What is claimed is:

1. A pharmaceutical composition in the form of an oral suspension of a normally unpalatable acidic drug, which is a quinolone-carboxylic acid derivative or a salt thereof or a naphthyridone carboxylic acid derivative or a salt thereof, which suspension is substantially devoid of bitter taste, which comprises particles of a readily soluble acidic drug which in solution has a bitter taste, and water for oral suspension, and one or more alkaline pH modifying agents mixed with the particles of drug which renders and maintains the drug in substantially insoluble form in the oral suspension, so that the bitter taste of the drug is masked without the use or need for polymer or wax coatings or microencapsulation wherein the pH modifying agents adjusts suspension pH to cause reduction in solubility or in-situ precipitation of the drug in the suspension.

2. The pharmaceutical composition as defined in claim 1 wherein the drug is a quinolone-carboxylic acid derivative or a salt thereof.

3. The pharmaceutical composition as defined in claim 1 wherein the drug is

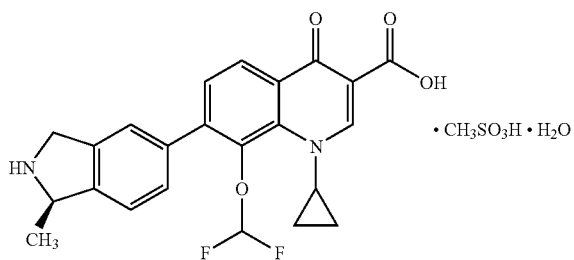

1-cyclopropyl-8-(difluoromethoxy)-7-[(1R)-1-methyl-2,3-dihydro-1H-5-isoindolyl]-4-oxo-1,4-dihydro-3-quinolinecarboxylic acid methanesulfonate monohydrate (des-quinolone).

4. The pharmaceutical composition as defined in claim 1 wherein the acidic drug is des-quinolone, norfloxacin, ciprofloxacin or ofloxacin.

5. The pharmaceutical composition as defined in claim 1 wherein said alkaline agent is one or more selected from the group consisting of L-arginine, L-lysine, sodium citrate and magnesium hydroxide.

6. The pharmaceutical composition as defined in claim 1 wherein said composition further optionally includes one or more antioxidants, glidants, and/or suspending agents.

7. The pharmaceutical composition as defined in claim 1 comprising from about 10 mg to about 600 mg (per 5 ml of suspension) of readily water-soluble acidic drug, from about 3 mg to about 200 mg of an alkaline pH modifying agent, and sufficient amount of water to provide 5 ml of suspension.

8. The pharmaceutical composition as defined in claim 1 in the form of an oral suspension comprising per 5 ml of constituted suspension, which comprises
 drug in an amount within the range from about 10 mg to about 600 mg,
 pH modifying agent in an amount within the range from about 3 mg to about 200 mg,
 antioxidant in an amount within the range from about 0 to about 20 mg,
 glidant in an amount within the range from about 0 to about 100 mg,
 suspending agent in an amount within the range from about 0 to about 24 mg, and
 water as necessary to provide 5 ml of constituted suspension.

9. The pharmaceutical composition as defined in claim 8 wherein the drug is
 1-cyclopropyl-8-(difluoromethoxy)-7-[(1R)-1-methyl-2,3-dihydro-1H-5-isoindolyl]-4-oxo-1,4-dihydro-3-quinolinecarboxylic acid methanesulfonate monohydrate, the pH modifying agent is L-arginine, the antioxidant is sodium bisulfite, the glidant is silicon dioxide and the suspending agent is sodium carboxymethyl cellulose.

10. A method for preparing an oral suspension of a drug which is substantially free of bitter taste, which comprises providing a readily water soluble drug which in solution has a bitter taste, which drug is a quinolone-carboxylic acid derivative or a salt thereof or a naphthyridone carboxylic acid derivative or a salt thereof, mixing the drug with a one or more alkaline pH modifying agents capable of generating an environment in water which causes reduction in solubility or in-situ precipitation of the drug, and mixing the drug and alkaline pH modifying agents with water to form an oral suspension which is essentially free of bitter taste, without the use or need for polymer or wax coating or microencapsulation.

11. A method for masking the bitter taste or otherwise unpalatable taste of a water-soluble drug for oral administration, which comprises providing a readily water-soluble drug in particulate form, which drug is a quinolone-carboxylic acid derivative or a salt thereof or a naphthyridone carboxylic acid derivative or a salt thereof, mixing the drug with one or more alkaline pH modifying agents, and water, whereby the pH modifying agent provides a pH environment which renders and maintains the drug substantially insoluble in suspension so that the bitter taste of the drug is masked and/or substantially reduced, upon oral administration, without the use or need for polymer or wax coatings or microencapsulation.

12. The method as defined in claim 11 wherein said drug is des-quinolone and the pH modifying agent is selected from the group consisting of L-arginine, L-lysine, sodium citrate and magnesium hydroxide.

13. An oral suspension of des-quinolone
 comprising des-quinolone,
 a pH modifying agent,
 optional excipients and water for suspension,
the des-quinolone being rendered and maintained substantially insoluble in the water for suspension, whereby the oral suspension is substantially free of bitter taste without the use or need for polymer or wax coating or microencapsulation.

* * * * *